(12) United States Patent
Nakamura et al.

(10) Patent No.: US 7,308,826 B2
(45) Date of Patent: Dec. 18, 2007

(54) MUSCULAR STRENGTH ACQUIRING METHOD AND DEVICE BASED ON MUSCULOSKELETAL MODEL

(75) Inventors: Yoshihiko Nakamura, Tokyo (JP);
Katsu Yamane, Tokyo (JP); Yusuke Fujita, Tokyo (JP); Akihiko Murai, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 11/629,694

(22) PCT Filed: Jun. 10, 2005

(86) PCT No.: PCT/JP2005/010645

§ 371 (c)(1),
(2), (4) Date: Feb. 9, 2007

(87) PCT Pub. No.: WO2005/122900

PCT Pub. Date: Dec. 29, 2005

(65) Prior Publication Data

US 2007/0256494 A1   Nov. 8, 2007

(30) Foreign Application Priority Data

Jun. 16, 2004   (JP) ............................. 2004-178063

(51) Int. Cl.
*A61B 5/22*   (2006.01)

(52) U.S. Cl. .................................................. 73/379.01
(58) Field of Classification Search ............. 73/379.01, 73/379.02; 703/11; 600/587
See application file for complete search history.

(56) References Cited

U.S. PATENT DOCUMENTS 7,251,593 B2* 7/2007 Dariush et al. ............... 703/11
2006/0287612 A1* 12/2006 Duda et al. .................. 600/587

* cited by examiner

*Primary Examiner*—Jewel Thompson
(74) *Attorney, Agent, or Firm*—Ladas & Parry LLP

(57) ABSTRACT

The present invention provides a method capable of acquiring a physically and physiologically valid muscular strength from motion data based on a musculoskeletal model. The present invention relates to a method for obtaining muscular tension by performing inverse dynamics calculation of a musculoskeletal model. The method comprises a step for optimizing a contact force $\tau_C$ received from an environment using acquired floor reaction force data and a step for optimizing the muscle tension f using acquired motion data, acquired myogenic potential data, and optimized contact force. The motion data, reaction force data and myogenic potential data can be measured at the same time by a behavior capture system.

22 Claims, 4 Drawing Sheets

MUSCULAR STRENGTH ACQUIRING METHOD AND DEVICE BASED ON MUSCULOSKELETAL MODEL

TECHNICAL FIELD

The present invention relates to a method capable of acquiring a physically and physiologically valid muscular strength from motion data based on a musculoskeletal model. "Physically valid" means herein that a muscular tension satisfies a dynamic equation. "Physiologically valid" means that a muscular tension is actually generated by a human.

BACKGROUND ART

The somatic sensation is a sensation perceived by the receptors in the superficial layer and deeper tissue of the body. It is divided into tactile cutaneous sensation and deep sensation generated by motor organs such as muscles and tendons. Deep somatic sensation accompanying exercises plays an important part in medical fields such as rehabilitation and surgery, and also sports science. Additionally, it is considered that machines should have the capability of estimating the somatic sensation of the human body for smooth interaction between people and machines.

The first step in estimating the somatic sensation from motions is to estimate the muscle force from motion data. Conventionally, there have been many studies to estimate muscular force from motion data. However, in these studies the muscular force was calculated using the geometrical nature of the motion such as the physiological model of muscles and percentage change of muscular length. They did not consider whether the motion could be realized with the obtained muscular force. A method for calculating the muscular force considering dynamic validness includes the AnyBody Project (J. Rasmussen, M. Damsgaard, E. Suruma, S. T. Christensen, M. de Zee, and V. Vondrak: "AnyBody-a software system for ergonomic optimization," Fifth World Congress on Structural and Multidisciplinary Optimization, 2003) and studies of the inventors (Y. Nakamura, K. Yamane, I. Suzuki, and Y. Fujita: "Dynamic Computation of Musculoskeletal Human Model Based on Efficient Algorithm for Closed Kinematic Chains," Proceedings of International Symposium on Adaptive Motion of Animals and Machines, SaP-I-2, 2003). However, they did not consider the physiological validness. The number of muscular tensions physically valid for a single motion is innumerable. However, they are not always physiologically valid. Conventionally, there have been methods for calculating muscular tensions that are satisfactory in either a physical manner or physiological manner, but there has been no method for calculating the muscular tension satisfying the physical and physiological characteristics at the same time.

Patent document: Japanese published unexamined application 2003-339673

DISCLOSURE OF THE INVENTION

The present invention provides a method and a device capable of acquiring a physically and physiologically valid muscular strength from motion data based on a musculoskeletal model.

A technical means adopted by the present invention to solve the problems shown above is a method and a device for obtaining muscular tension by performing inverse dynamics calculation of a musculoskeletal model using the equation shown below.

$$\tau_G = J^T f + J_C^T \tau_C$$

where $\tau_G$ is generalized force, J is Jacobian of muscles, tendons and ligaments and $J_c$ is Jacobian of contact point.

The present invention obtains muscular tension by providing reaction force data, motion data and myogenic potential data to the above equation and optimizing a contact force $\tau_C$ and muscle tension f.

In a preferred mode, a method for calculating muscle tension comprises a first step for optimizing a contact force $\tau_C$ received from an environment using acquired reaction force data and a second step for optimizing the muscle tension f using acquired motion data, acquired myogenic potential data, and optimized contact force.

In a preferred mode, the motion data are obtained by a motion capture system. In a preferred example, a motion capture system for acquiring motion data is an optical motion capture system. A motion capture method used for acquiring motion data is not limited to an optical type. In one mode, reaction force data are acquired with a force sensor. If used reaction force data are ground reaction force data, in a preferred mode, the ground reaction force data are acquired with a force plate. Ground reaction force data may be acquired with a force sensor attached to the soles of a subject's feet. In a preferred mode, the myogenic potential data are acquired with an electromyograph. In a preferred mode, the motion data, ground reaction force data and myogenic potential data are measured at the same time.

In a preferred mode, contact force is optimized by quadratic programming using a certain objective function, and inequality constraint conditions. Muscular tension is optimized by linear programming. In the above equation, generalized force $\tau_G$ and Jacobian J of length of muscle, tendon and ligament concerning generalized coordinate can be calculated by acquired motion data. Jacobian $J_C$ of a contact point can be calculated by acquired reaction force data.

In a preferred mode, the present invention comprises means for storing the obtained motion data and calculated muscular tension by linking them with each other.

In addition to the method and device, the present invention can also provide a computer program for causing a computer to operate to acquire muscular tension by performing inverse dynamics calculation of musculoskeletal model.

In the present invention, physically and physiologically valid muscular tension can be calculated by performing inverse dynamics calculation and optimization calculation using motion data, measurement data of myogenic potential data and ground reaction force. If muscular tension is calculated for many tasks and subjects using this method, and similarity of antagonistic muscles is found for each task, muscular tension can be estimated to a certain degree even if there is no myogenic potential and ground reaction force data.

DETAILED DESCRIPTION

The present invention provides a method for calculating a physically and physiologically valid muscular strength from motion data obtained by motion capture and information about myogenic potential and ground reaction force measured at the same time. Human musculoskeletal model consists of many muscles and is generally a redundant drive system. Therefore, muscle force cannot be determined uniquely. If standard usages of muscles in various motions are compiled in a database by using this method, muscular force may be estimated even if myogenic potential and ground reaction information are not acquired.

In embodiments of the present invention, a device for acquiring muscle tension comprises a plurality image capturing means (a camera) to capture subjects with marks affixed, ground reaction force measuring means (a force plate), myogenic potential measuring means (an electromyograph) and one or more computers. A computer comprises a processing unit, an input device, an output device, a display device and a memory device storing various data.

In this embodiment, a behavior capture system measures electromyogram (EMG) and ground reaction force, as well as motion data, at the same time. Physically and physiologically valid muscular strength is acquired by considering them in optimization of muscular strength. The behavior capture system is disclosed in Seri, Yamane, Nakamura: "Simultaneous and real-time measurement of conscious actions with behavior capture system", Lecture meeting on robotics and mechatronics, The Japan Society of Mechanical Engineers, proceedings 01, 1P1-H7, 2001.

The behavior capture system is a system for measuring interactive information of human behavior in addition to a motion capture system that measures only human whole-body motions. The behavior capture system can measure and process information input to humans (point of gaze), information output from humans (behavior, ground reaction force, brain waves and internal human information) in simultaneous and in a real-time manner. The information can be reviewed in a 3D manner on a screen. In the present invention, the behavior capture system measures the motion capture data (motion data), electromyogram (EMG), and ground reaction force at the same time. A physically and physiologically valid muscular strength is acquired by using the data in optimization of muscular strength.

Figure 1:
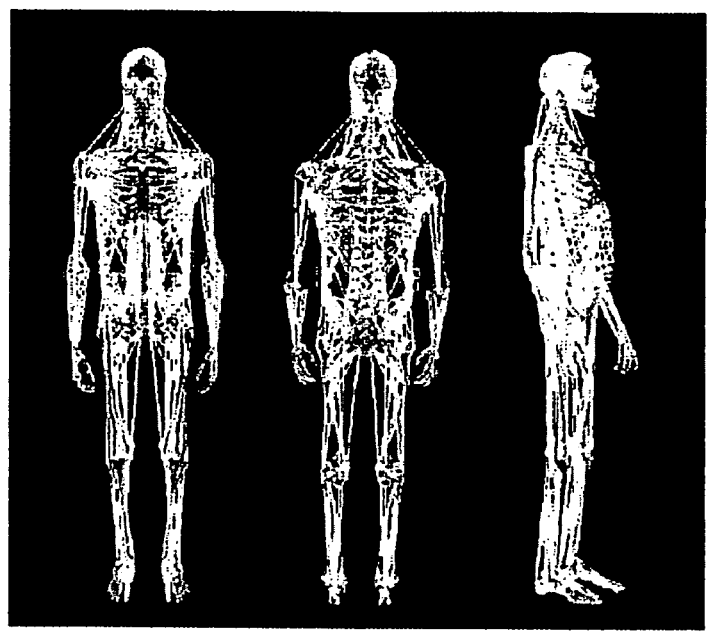
FIG. 1 is a drawing showing a human muscular skeletal model.

Musculoskeletal model and inverse dynamics of musculoskeletal, which are prerequisites for calculating muscular strength, will now be explained. As a human musculoskeletal model, a model developed by a group of inventors consisting of a total 547 of muscles, tendons and ligaments, and a bone structure with a degree of freedom of 155 is used (FIG. 1). In this model; muscles, tendons and ligaments are expressed as a wire having no thickness. Kinetic properties such as via-points and divergence points are based on anatomical documents. Details of the musculoskeletal model are disclosed in Suzuki, Yamane, Taya, Kurihara, Nakamura: "Human dynamic computation based on detailed human body model using high-speed kinetics calculations", collected manuscripts, the 20th academic lecture of The Robotics Society of Japan, 3C14, 2002, and Japanese published unexamined applications 2003-339673, and 2004-13474. Data of musculoskeletal model are stored in the memory device of the device of the present invention.

A designed detailed human model consists of bones grouped with appropriate detail, and network among muscles, tendons and ligaments covering areas between bones. Each element has the following characteristics. A bone is a rigid-body link having mass. A muscle is a wire that generates tension positively and is relatively elastic. A tendon is a wire that generates tension passively and is relatively inelastic. Additionally, a tendon transmits the muscle tension to distant parts by connecting to muscles. A ligament is a wire that generates tension passively and is relatively inelastic. A ligament connects bones, and constrains relative motion among bones.

Muscles, tendons and ligaments are modeled as wires that pass through start points, end points and zero or more routing points. A routing point is established in cases where a muscle gets caught in a part of a bone, and a model where a tendon is constrained by a tendon sheath. In general, the start point, end point and routing point are fixed on bones. A virtual link is established at a bifurcation point to describe diverging muscles and ligaments. In this way, a wire starts from a start point, passes zero or more routing points and ends at an end point.

Inverse dynamics will now be explained. In inverse dynamics, the tension of muscles, tendons and ligaments to realize a motion is calculated based on motion data acquired from the motion measurements or motion generation such as choreography. The flow of inverse dynamics calculation includes: 1. Calculation of joint torque by inverse dynamics of a rigid-body link system; 2. Calculation of Jacobian for joint value of wire length; and 3. Conversion of joint torque to wire tension.

The inverse dynamics of this model can be formulated as follows. First, generalized force TG required for a given motion is calculated. If generalized coordinate 0 is a joint angle of a bone structure, the generalized force corresponds to joint torque. Therefore, the generalized force (joint torque) can be calculated using Newton-Euler Formulation. In this case, assuming that the six degrees of freedom of the hip link are also driven, $\tau_G$ includes six axial forces acting on the hip link. Then, Jacobian J of the length of muscles, tendons and ligaments relating to generalized coordinates is calculated. In other words, if the length of muscles, tendons and ligaments is made aligned vector 1, J is expressed by the following equation.

$$J \triangleq \frac{\partial l}{\partial \theta_G} \tag{1}$$

Detailed methods for calculating Jacobian J are disclosed in Suzuki, Yamane, Taya, Kurihara, Nakamura: "Human dynamic computation based on detailed human body model using high-speed kinetics calculations", collected manuscripts, the 20th academic lecture of The Robotics Society of Japan, 3C14, 2002, in Japanese published unexamined application 2003-339673, and in D. E. Orin and W. W. Schrader: "Efficient Computation of the Jacobian for Robot Manipulators," International Journal of Robotics Research, vol. 3, no. 4, pp. 66-75, 1984.

Using Jacobian J, the relationship between generalized force, tension vectors f of muscles, tendons and ligament, and contact force received from environment, is described as $$\tau_G = J^T f + \sum J_{Ci}^T \tau_{Ci} \quad (2)$$

where $\tau_{Ci}$ is a contact force at the contact point i, $J_{Ci}$ is Jacobian at the contact point i.

Jacobian $J_c$ of a contact point is defined by the following equation. In the following equation, pc is a vector or a parameter expressing the position and posture of a contact point. The method for calculating Jacobian is disclosed in the documents shown above.

$$J_c \triangleq \frac{\partial p_c}{\partial \theta_G} \quad (1')$$

Terms concerning contact force in equation (2) are rearranged as follows:

$$\tau_G = J^T f + J_C^T \tau_C \quad (3)$$

The inverse dynamics calculation of the musculoskeletal model is to obtain f and $\tau_C$ satisfying equation (3) from $\tau_G$. Generally, in the musculoskeletal model, the number of muscles is larger compared to number of degrees of freedom. Therefore, f is not determined uniquely. If two or more links contact the environment, the contact forces become indeterminate. It is required to perform optimization by some criteria to determine these values.

Optimization will now be explained. First, objective function and restraint conditions are mentioned considering measured values of contact force and electromyogram (EMG), followed by description of formulation of optimization problem and solution.

The contact force will now be explained. As mentioned above, the generalized force $\tau_G$ includes six axial forces acting on the hip link that is not actually driven. The muscular strength that is an internal force cannot generate a corresponding force. Therefore, it is substituted by the contact force. The rows corresponding to six degrees of freedom of the hip link extracted from equation (3) is as follows:

$$E_{hip}\tau_G = E_{hip} J_C^T \tau_C \quad (4)$$

where $E_{hip}$ is a matrix that extracts required rows. If the number of contacted links is one, unique solution exists. However, if the number is two or more, it will become indeterminate.

In the present invention, this problem is solved by using ground reaction force data measured with a force plate. Therefore, the following terms are included in the optimization objective function.

$$|K_C \tau_C - \tau^*_C|^2 \quad (5)$$

where $\tau^*_C$ is a measured contact force, and $K_C$ is a matrix that maps the contact forces acting on each link into a coordinate system of measured contact forces. For example, if a plurality of links exist on a force sensor, the sum of the ground reaction forces acting on those links is measured, and so is converted by $K_C$.

The contact force shall satisfy a certain condition regarding the vertical force, center of pressure, friction force, etc. Among them, the vertical force is handled by incorporating the following inequality constraint condition.

$$E_{vert}\tau_C \geq 0 \quad (6)$$

where $E_{vert}$ is a matrix that extracts the vertical components from $\tau_C$. Other conditions are considered approximately by incorporating the following equation in the objective function.

$$|\tau_C|^2 \quad (7)$$

Figure 2:
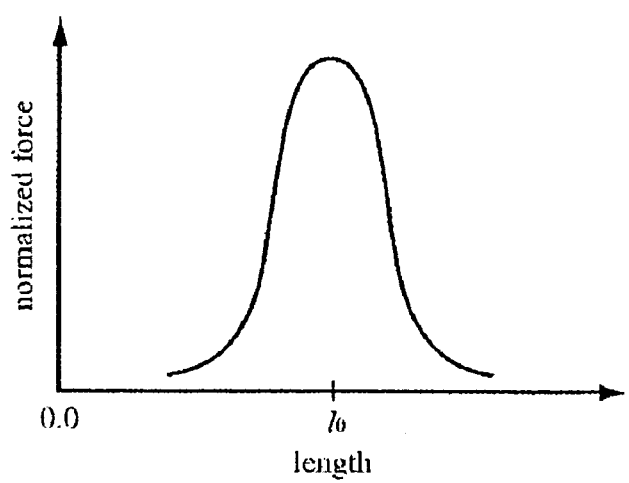
FIG. 2 is a chart showing the relationship between muscular length and maximum isometric muscular strength.
Figure 3:
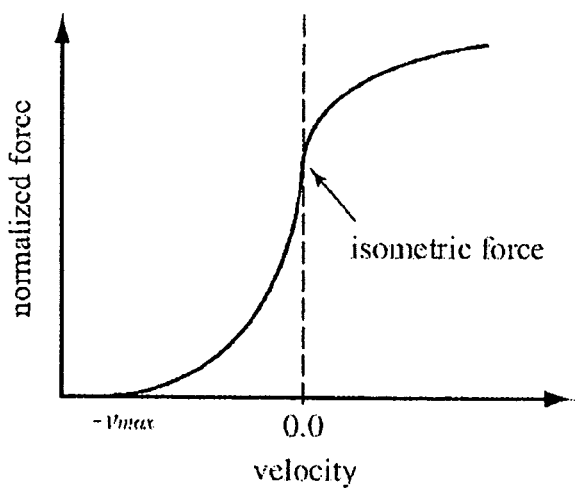
FIG. 3 is a chart showing the relationship between change rate of muscular length and maximum muscle tension.

Electromyogram (EMG) will now be explained. In the present invention, the Stroeve muscle model that formulates the muscle model of Hill and Wilkie is used. In this model, the relationship between muscle length and maximum isometric muscular strength is expressed as FIG. 2. The relationship between change rate of muscle strength and maximum muscle tension is shown in FIG. 3. At the maximum contraction velocity $v_{max}$, the muscular strength is zero. The maximum muscle tension when the muscle length does not change corresponds to the maximum isometric muscular strength. A muscle extends when a force larger than the maximum isometric muscular strength is applied.

IEMG (the integrated EMG), which is a value measured by an electromyograph integrated by a certain time interval, expresses the activity factor u of a motor nerve. The relationship between u and muscle activity factor a is expressed by the following equation.

$$\dot{a} = \frac{u - a}{T} \quad (8)$$

where T is a parameter expressing time delay. The relationship between a and muscle tension f* is expressed by the following equation.

$$f^* = a F_l(l) F_v(\dot{l}) F_{max} \quad (9)$$

where $F_{max}$ is a function to express the maximum muscle tension. $F_l(l)$ and $F_v(\dot{l})$ are functions expressing the relationship between normalized muscular strength and muscular length, and change rate of muscular length, respectively.

$F_l(l)$ corresponds to FIG. 2 and is approximated by the Gaussian function in the following equation.

$$F_l(l) = \exp\left\{-\left(\frac{l - l_0}{K_l}\right)^2\right\} \quad (10)$$

$F_v(\dot{l})$ corresponds to FIG. 3 and is approximated by the following equation.

$$F_v(l) = \begin{cases} 0 & (i \le -v_{max}) \\ \dfrac{V_{sh}(v_{max}+i)}{V_{sh}v_{max}-i} & (-v_{max} \le i \le 0) \\ \dfrac{V_{sh}V_{shl}v_{max}+V_{ml}i}{V_{sh}V_{shl}v_{max}+i} & (0 \le i) \end{cases} \quad (11)$$

where $K_l$, $V_{sh}$, $V_{shl}$, and $V_{ml}$ are constants. Values mentioned by Stroeve are used here.

$n_{ch}$ muscular strength values f* are obtained by using an electromyograph with $n_{ch}$ channels. As for the surface electromyograph used in the present invention, an electromyogram (EMG) measured in a channel does not always correspond to a muscle in the musculoskeletal model. In some cases, the sum of potential of several muscles is measured. Considering this case, the measured value of electromyogram (EMG) shall be considered by incorporating the following equation in the objective function with the matrix $K_F$ that makes f and measured value correspond to each other.

$$|K_F f - f^*| \quad (12)$$

A muscle, tendon and ligament can only generate force in the direction of tension. Therefore, the following inequality constraint is applied.

$$f \le 0 \quad (13)$$

Optimization calculation will now be explained. Optimization calculation is performed in the following two phases by using equations shown above.

Step 1: Optimization of contact force using quadratic programming

Step 2: Optimization of muscle tension by using linear programming.

First, in the step 1, $\tau_C$ that satisfies inequality constraint condition $$E_{vert}\tau c \ge 0 \quad (14)$$

and minimizes the objective function $$Z = w_H |E_{hip}\tau_G - E_{hip}J_C^T\tau_C|^2$$
$$+ w_C |K_C \tau_c - \tau_C^*|^2 + |\tau_C|^2 \quad (15)$$

is calculated, where $w_H$ and $w_C$ are weighting parameters. The first term in the objective function has the effect of reducing the error of equation (4). $w_H = 1 \times 10^8$ and $w_c = 10$ are used here.

When a contact force is acquired by the calculations shown above, the generalized force that should be generated by the muscle tension can be calculated by the following equation.

$$\tau'_G = \tau_G - J_C^T \tau_C = J^T f. \quad (16)$$

In the step 2 of the optimization, $\delta_f$, $\delta_\tau$ and f that satisfy the inequality constraint condition $$-\delta_f \le K_F f - f^* \le \delta_f \quad (17)$$

$$E_{mtl} f \le 0 \quad (18)$$

$$\delta_f \ge 0 \quad (19)$$

$$-\delta_\tau \le \tau'_G - J^T f \le \delta_\tau \quad (20)$$

$$\delta_\tau \ge 0 \quad (21)$$

and minimize the objective function $$Z = a_f^T \delta_f + a_\tau^T \delta_\tau \quad (22)$$

are obtained by using $\tau'_G$, where $a_f$ and $a_\tau$ are constant vectors with positive components. The muscle tension can be approximated to the measured value by minimizing equation (22) based on the equation (17). Equation (20) reduces the error of equation (16) induced from the dynamics equation. Therefore, dynamic consistency is also considered.

Modifications to muscular strength optimization calculation will now be explained. The deviation from average muscle tension of a muscle group is added to the objective function for optimizing the muscular strength. In other words, the foregoing objective function $$Z = a_f^T \delta_f + a_\tau^T \delta_\tau \quad (22)$$

is replaced by $$Z = a_f^T \delta_f + a_\tau^T \delta_\tau + a_m^T \delta_m \quad (23)$$

where $a_m$ is a constant vector with positive components. $\delta_m$ is a vector that satisfies the following restraints.

$$-\delta_m \le E_G f \le \delta_m \quad (24)$$

$$0 \le \delta_m \quad (25)$$

$E_G$ is a matrix for calculating the difference between the average value of muscle tensions belonging to each of pre-defined muscle group and each muscle tension. They are calculated in a method shown below.

Assuming that a class including the number of muscles belonging to muscle group k is $G_k$, the average $\bar{f}_k$ (with bar) of muscular tension belonging to the muscle group k is obtained from $$\bar{f}_k = \frac{1}{n_k} \sum_{i \in G_k} f_i \quad (26)$$

where $n_k$ is a number of muscles belonging to the muscle group k. Consequently, the difference between the tension of the muscle $n (n \in G_k)$ and average of muscles belonging to muscle group k is calculated by $$\Delta f_{nk} = \bar{f}_k - f_n = E_{Gkn} f \quad (27)$$

where $E_{Gkn}$ is a horizontal vector with the same number of elements as the number of muscles. The i-th element is $(1 - n_k/n_k)$ for I=n, $1/n_k$ for i≠n and i∈$G_k$ and 0 in other cases. Finally, $E_G$ is obtained by vertically accumulating $E_{Gkn}$ of muscles contained in all muscle groups.

In the conventional calculating method using linear programming, muscles that mainly generate tensions in the muscles (cooperative muscles) that have the similar role (elbow joint extension, etc) change discontinuously. As a result, the method has a problem that the tension of each muscle changes rapidly. Muscle tension is averaged among cooperation muscles and smoother tension change is obtained by changing the objective function as shown above.

Experimental examples will now be explained. Motion capture markers and electrodes for 16 channels were affixed to both legs of a subject. EMG, ground reaction force, and motion capture data for squat exercise were obtained at the same time. Two force plates were used for measuring the ground reaction force. The force and moment applied to left and right leg were measured independently. As a result, EMG and ground reaction force data per 1 ms and motion capture data per 33 ms were acquired.

Figure 4:
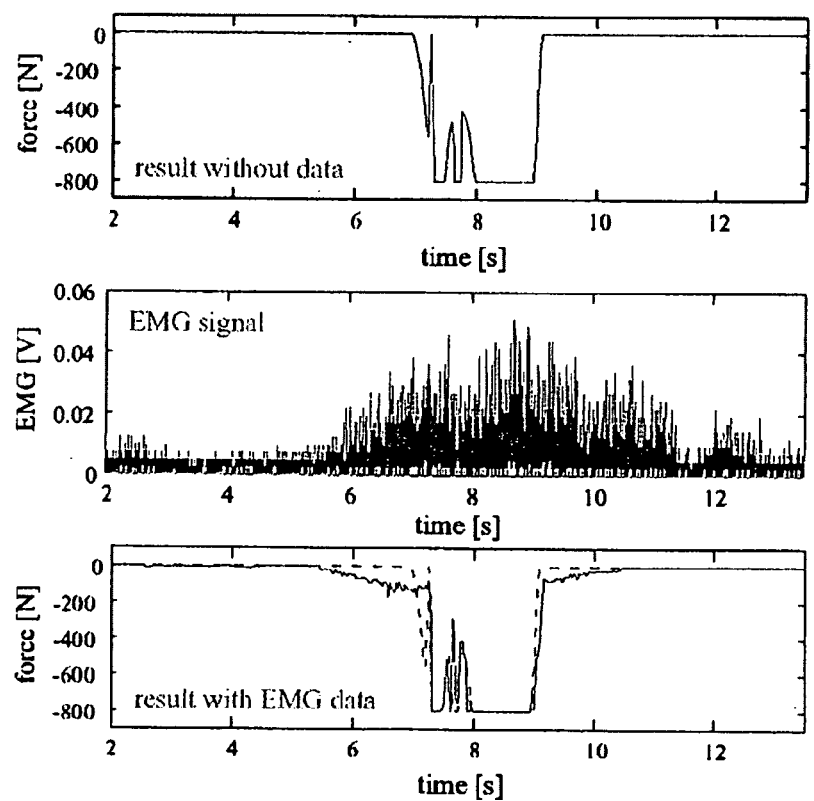
FIG. 4 is a chart showing the calculated and measured values of right lateral great muscle. The upper row shows the calculated results when no EMG and ground reaction force data were used. The middle row shows the measured EMG signal. The lower row shows the calculated results when EMG signal is used.

The upper row of FIG. 4 shows the result of optimization for the right lateral great muscle without using the data of EMG and ground reaction force assuming $\tau^*_C=0$ and $f^*=0$. Initial rise of muscle tension is delayed compared to the EMG data in the middle row of FIG. 4, indicating that the muscle started activity before starting actual motion. The pattern similar to the measured values is obtained if actual EMG data is used for calculation (lower row of FIG. 4). The computation time required for optimizing the muscle tension is 0.81 s on average.

Figure 5:
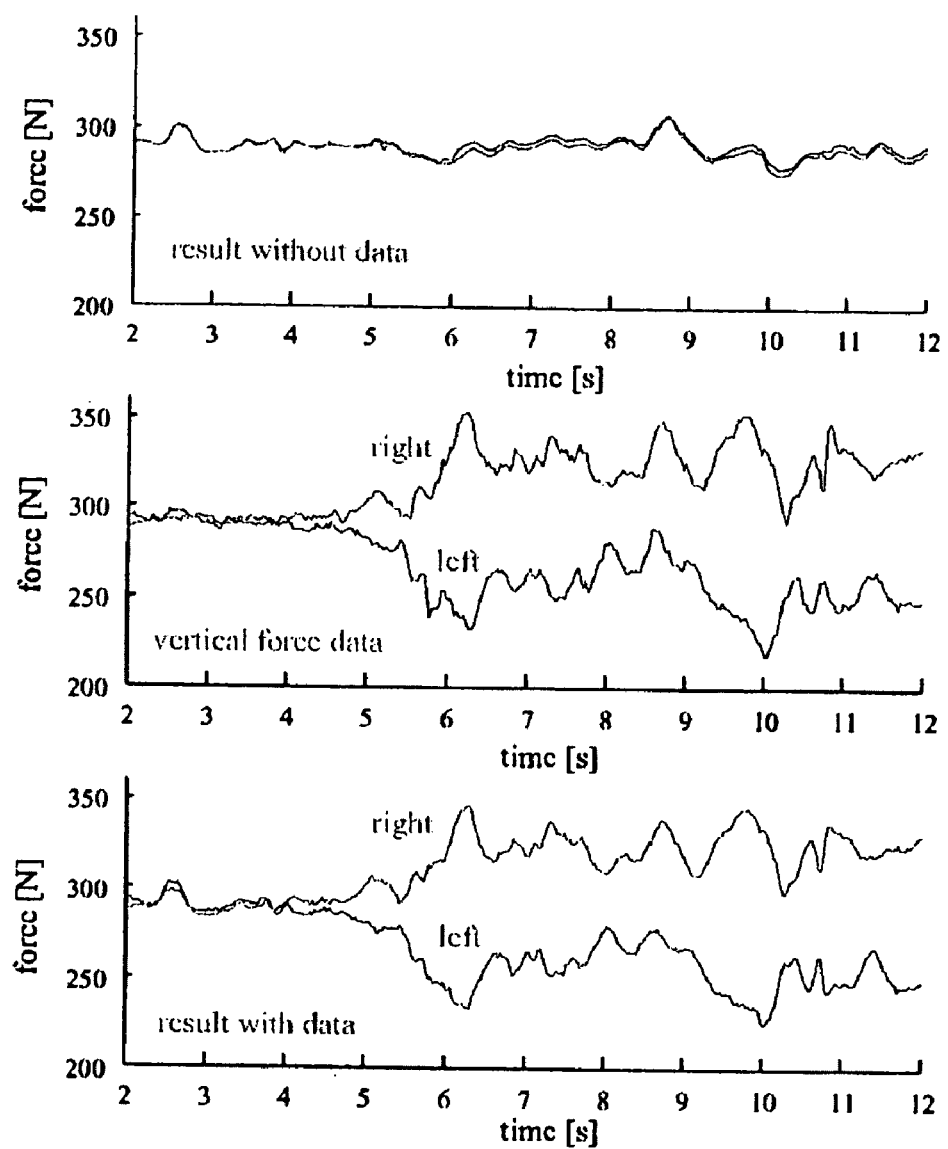
FIG. 5 is a chart showing the calculated and measured value of elements of ground reaction force in the vertical direction. The upper row shows the calculation result when no EMG and ground reaction force are used. The middle row shows the elements of measured ground reaction force in the vertical direction. The lower row shows the calculation result when ground reaction force data are used.

If optimization is performed without using the ground reaction force data, the ground reaction force as shown in the upper row of FIG. 5 is acquired because the force is distributed evenly to left and right. On the other hand, with the measured value of elements of the ground reaction force in the vertical direction, the force distribution for left and right legs is uneven after starting activity as shown in the middle row of FIG. 5. Distribution similar to measured value as shown in the lower row of FIG. 5 is also acquired by considering measured data. When both legs were in contact with the ground, the computation time required for optimizing the ground reaction force was 8.8 ms on average.

Figure 6:
FIG. 6 is a chart visually showing the result for the case where no EMG and ground reaction force data were used (upper row) and where EMG and ground reaction force data were used (lower row).

FIG. 6 shows the visualized results of the case where no EMG and ground reaction force data was used (upper row) and the case where EMG and ground reaction force data were used (lower row). The larger muscle tension is indicated in black not white. It indicates that unbalance between left and right reaction force is reflected in the muscle tension if ground reaction force data are considered.

In the present invention, a physically and physiologically valid muscular strength can be calculated by performing inverse dynamics and optimized calculation by using motion data, and measured data of EMG and ground reaction force. If muscular tension is calculated for many tasks and subjects, and similarity of antagonistic muscles is found for each task, muscular tension can be estimated to a certain degree even if there is no EMG and ground reaction force data.

The invention claimed is:

1. A method for obtaining muscular tension by performing inverse dynamics calculation of a musculoskeletal model, said method comprising:
   obtaining muscular tension by providing reaction force data, motion data and myogenic potential data to the following equation and by optimizing a contact force $\tau_C$ and muscle tension f.

$$\tau_G = J^T f + J_C^T \tau_C$$

where $\tau_G$ is generalized force, J is Jacobian of muscles, tendons and ligaments and $J_C$ is Jacobian of contact point.

2. A method for obtaining muscular tension by performing inverse dynamics calculation of a musculoskeletal model by using the following equation $$\tau_G = J^T f + J_C^T \tau_C$$

where $\tau_G$ is generalized force, J is Jacobian of muscles, tendons and ligaments and $J_C$ is Jacobian of contact point, said method comprising:
   optimizing a contact force $\tau_C$ received from an environment using acquired reaction force data; and
   optimizing the muscle tension f using acquired motion data, acquired myogenic potential data, and optimized contact force.

3. The method of claim 2, wherein the motion data are obtained by a motion capture system.

4. The method of claim 2, wherein reaction force data are acquired with a force sensor.

5. The method of claim 2, wherein the myogenic potential data are acquired with an electromyograph.

6. The method of claim 2, wherein the motion data, reaction force data and myogenic potential data are measured at the same time.

7. The method of claim 2, wherein said optimizing a contact force $\tau_C$ comprises:
   calculating $\tau_C$ that minimizes the objective function $$Z = w_H |E_{hip}\tau_G - E_{hip}J_C^T \tau_C|^2$$
   $$+ w_C |K_C \tau_C - \tau_C^*|^2 + |\tau_C|^2$$

subject to the inequality constraint condition $$E_{vert}\tau_C \geq 0$$

where $E_{vert}$ is a matrix that extracts the vertical forces from $\tau_C$, $\tau_C^*$ is a measured contact force, $E_{hip}$ is a matrix that extracts required rows, and $w_H$ and $w_C$ are weighting parameters.

8. The method of claim 2, wherein said optimizing a muscle tension f comprises:
   calculating $\delta_f$, $\delta_\tau$ and f that minimize the objective function $$Z = a_f^T \delta_f + a_\tau^T \delta_\tau$$

subject to the inequality constraint condition $$-\delta_f \leq K_F f - f^* \leq \delta_f$$
   $$E_{mif} f \leq 0$$
   $$\delta_\tau \geq 0$$
   $$-\delta_\tau \leq \tau'_G - J^T f \leq \delta_\tau$$
   $$\delta_\tau \geq 0$$

where f* are muscular strength values, $K_F$ is a matrix that makes f and measured value correspond to each other, and $a_f$ and $a_\tau$ are constant vectors with positive components.

9. The method of claim 8, said inequality constraint condition further comprising $$-\delta_m \leq E_G f \leq \delta_m$$
   $$0 \leq \delta_m$$

and said objective function being replaced with $$Z = a_f^T \delta_f + a_\tau^T \delta_\tau + a_m^T \delta_m$$

where $a_m$ is a constant vector with positive components.

10. The method of claim 2, said method further comprising storing the obtained motion data and calculated muscle tension linking with each other as database.

11. An apparatus for obtaining muscular tension based on a musculoskeletal model comprising a processing unit and a memory device,
    said memory device storing reaction force data, motion data, myogenic potential data and the following equation $$\tau_G = J^T f + J_C^T \tau_C$$

where $\tau_G$ is generalized force, J is Jacobian of muscles, tendons and ligaments and $J_C$ is Jacobian of contact point,
    said processing unit obtaining muscular tension by providing reaction force data, motion data and myogenic potential data to the following equation and by optimizing a contact force $\tau_C$ and muscle tension f.

12. The apparatus of claim 11, said processing unit is adapted to perform optimization of a contact force $\tau_C$ received from the environment using acquired ground reaction force data and optimization of the muscle tension f using acquired motion data, acquired myogenic potential data, and optimized contact force.

13. The apparatus of claim 11, said memory device store inequality constraint condition and objective function that is used for optimization of a contact force $\tau_C$ and muscle tension f.

14. The apparatus of claim 13, wherein said objective function for optimization of a contact force $\tau_C$ is $$Z=w_H|E_{hip}\tau_G-E_{hip}J_C^T\tau_C|^2$$
$$+w_C|K_C\tau_C-\tau_C^*|^2+|\tau_C|^2$$

and said inequality constraint condition is $$E_{vert}\tau_C \geq 0$$

where $E_{vert}$ is a matrix that extracts the vertical forces from $\tau_C$, $\tau_C^*$ is a measured contact force, $E_{hip}$ is a matrix that extracts required rows, and $w_H$ and $w_C$ are weighting parameters.

15. The apparatus of claim 13, wherein said the objective function for optimization of a muscle tension f is $$Z=a_f^T\delta_f+a_\tau^T\delta_\tau$$

and said the inequality constraint condition is $$-\delta_f \leq K_F f - f^* \leq \delta_f$$
$$E_{mtl}f \leq 0$$
$$\delta_f \geq 0$$
$$-\delta_\tau \leq \tau_G - J^T f \leq \delta_\tau$$
$$\delta_\tau \geq 0$$

where f* are muscular strength values, $K_F$ is a matrix that makes f and measured value correspond to each other, and $a_f$ and $a_\tau$ are constant vectors with positive components.

16. The apparatus of claim 15, said inequality constraint condition further comprising $$-\delta_m \leq E_G f \leq \delta_m$$
$$0 \leq \delta_m$$

and said objective function being replaced with $$Z=a_f^T\delta_f+a_\tau^T\delta_\tau+a_m^T\delta_m$$

where $a_m$ is a constant vector with positive components.

17. The apparatus of claim 11 further comprising a motion capture system for obtaining motion data.

18. The apparatus of claim 11 further comprising a force sensor for obtaining reaction force data.

19. The apparatus of claim 11 further comprising an electromyograph for obtaining myogenic potential data.

20. The apparatus of claim 11 further comprising means for linking the motion data and muscle tension and wherein linked motion data and muscle tension are stored in the memory device as database.

21. A computer program for causing a computer to operate as the following means to acquire muscular tension by performing inverse dynamics calculation of musculoskeletal model, means for storing reaction force data, motion data, myogenic potential data and the following equation $$\tau_G=J^T f+J_C^T \tau_C$$

where $\tau_G$ is generalized force, J is Jacobian of muscles, tendons and ligaments and $J_C$ is Jacobian of contact point, means for optimizing a contact force $\tau_C$ received from an environment using reaction force data, means for storing the optimized contact force, means for optimizing a muscular tension f by using motion data, myogenic potential data and the optimized contact force.

22. The program of claim 21 further causing a computer to operate as means for linking the motion data and muscle tension and wherein linked motion data and muscle tension are stored as database.

* * * * *